(12) United States Patent
Burdette et al.

(10) Patent No.: US 9,119,954 B2
(45) Date of Patent: *Sep. 1, 2015

(54) ULTRASOUND DEVICE FOR TREATMENT OF A TUMOR IN A REGION OF INTERVERTEBRAL DISC TISSUE

(71) Applicant: Acoustic MedSystems, Inc., Savoy, IL (US)

(72) Inventors: Everette C. Burdette, Savoy, IL (US); Dana Deardorff, Oakland, CA (US)

(73) Assignee: Acoustic MedSystems, Inc., Savoy, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/657,464

(22) Filed: Oct. 22, 2012

(65) Prior Publication Data
US 2013/0046208 A1 Feb. 21, 2013

Related U.S. Application Data

(63) Continuation of application No. 11/818,046, filed on Jun. 12, 2007, now Pat. No. 8,292,815, which is a continuation of application No. 10/230,949, filed on Aug. 29, 2002, now abandoned.

(60) Provisional application No. 60/315,841, filed on Aug. 29, 2001.

(51) Int. Cl.
*A61N 7/00* (2006.01)
*A61N 7/02* (2006.01)
*A61B 17/00* (2006.01)

(52) U.S. Cl.
CPC ......... *A61N 7/02* (2013.01); *A61B 2017/00261* (2013.01); *A61N 2007/0078* (2013.01)

(58) Field of Classification Search
CPC ............. A61B 2017/00261; A61B 2019/5276; A61B 18/1482; A61B 2018/00029; A61N 2007/0078; A61N 7/02
USPC .............. 600/439; 601/2, 3; 606/3, 21, 32, 41
See application file for complete search history.

(56) References Cited

U.S. PATENT DOCUMENTS

| | | | | |
|---|---|---|---|---|
| 5,471,988 | A * | 12/1995 | Fujio et al. | 600/439 |
| 5,549,638 | A * | 8/1996 | Burdette | 601/3 |
| 5,620,479 | A * | 4/1997 | Diederich | 601/3 |
| 6,254,553 | B1 * | 7/2001 | Lidgren et al. | 601/3 |
| 6,258,086 | B1 | 7/2001 | Ashley et al. | |
| 6,350,262 | B1 * | 2/2002 | Ashley | 606/32 |
| 6,514,249 | B1 | 2/2003 | Maguire et al. | |
| 6,575,969 | B1 | 6/2003 | Rittman, III et al. | |
| 6,673,063 | B2 | 1/2004 | Brett | |
| 6,878,155 | B2 | 4/2005 | Sharkey et al. | |

(Continued)

*Primary Examiner* — Baisakhi Roy
(74) *Attorney, Agent, or Firm* — Foley & Lardner LLP

(57) ABSTRACT

An ultrasound device and method for the treatment of intervertebral disc tissue for remediation of back pain. An applicator comprises a catheter and/or needle with a distal tip including one or more ultrasound transducer crystals. The crystals produce high-powered ultrasound energy that is transmitted and absorbed in the disc tissue. The resulting temperature elevation of the disc tissue shrinks the collagen fibers in the surrounding tissue, and/or destroying small nerves that may have invaded and innervated the surrounding degenerated tissue, and can provide increased structural integrity and disc support for the fragmented nucleus pulposus to relieve pressure on the spinal nerves.

23 Claims, 1 Drawing Sheet

(56) References Cited

U.S. PATENT DOCUMENTS

| | | |
|---|---|---|
| 6,929,640 B1 | 8/2005 | Underwood et al. |
| 6,980,862 B2 * | 12/2005 | Fredricks et al. ............... 607/99 |
| 7,331,956 B2 * | 2/2008 | Hovda et al. .................... 606/32 |
| 7,473,224 B2 * | 1/2009 | Makin ........................... 600/439 |
| 7,806,892 B2 * | 10/2010 | Makin et al. ....................... 606/3 |
| 8,292,815 B2 * | 10/2012 | Burdette et al. .............. 600/439 |
| 2002/0095144 A1 * | 7/2002 | Carl ................................ 606/21 |
| 2003/0013960 A1 | 1/2003 | Makin et al. |
| 2003/0163067 A1 * | 8/2003 | Lidgren ........................... 601/2 |
| 2005/0090816 A1 * | 4/2005 | McClurken et al. ............ 606/41 |
| 2007/0016062 A1 * | 1/2007 | Park et al. ..................... 600/459 |

* cited by examiner

ULTRASOUND DEVICE FOR TREATMENT OF A TUMOR IN A REGION OF INTERVERTEBRAL DISC TISSUE

CROSS-REFERENCE TO RELATED PATENT APPLICATIONS

This application is a continuation and claims priority from copending U.S. patent application Ser. No. 11/818,046 filed Jun. 12, 2007, which is a continuation of U.S. patent application Ser. No. 10/230,949 filed Aug. 29, 2002, which claims priority from U.S. Provisional Patent Application Ser. No. 60/315,841. The entire contents of all three applications are herein incorporated by reference in their entirety.

FIELD OF THE INVENTION

The present invention relates generally to ultrasound applicator devices. More particularly, the present invention relates to the structure, design and use of a minimally invasive ultrasound applicator device for the thermal treatment of a tumor in a region of intervertebral disc tissue.

BACKGROUND OF THE INVENTION

The concept of using heat to treat degenerated disc tissue is conventionally known. For example, the orthopedic company ORATEC Interventions, Inc. has developed and marketed a device for thermal spine treatment based on Intra-Discal Electro-Thermal (IDET) technology. IDET technology involves a minimally invasive catheter using RF induction of a hot-wire tip for thermal conduction.

While relatively straightforward in design and use, the ORATEC device is very limited in thermal capabilities and ultimately in treatment efficacy. The region of disc tissue that is heated with this device is quite small with a sharp temperature fall-off from the surface of the catheter tip (therapeutic temperature elevation in the tissue is estimated to be only 1-3 mm from the catheter). As a result, the treatment itself is likely limited in effectiveness for any given patient, simply because the volume of tissue that is heated is not large enough to produce a significant therapeutic effect (i.e., shrinkage of collagen fibers, destruction of invading nerves, and/or reduction of pressure on the spinal nerves).

Furthermore, the design and treatment approach of the IDET catheter is significantly limiting in the general treatment population—it is estimated that more than 50% of the potential treatment population is not even a candidate for this device therapy. This is due to the use of a flexible "navigable catheter" which must be circumnavigated around the disc border between the annulus and the nucleus, positioning the treatment tip back at the posterior region of the degenerated disc. This positioning is possible with a healthy or slightly degenerated disc because the fibers of the annulus help "steer" the catheter around the disc tissue. However, with greater disc degeneration, this positioning is not possible because of the tissue degradation; there is no structure for the catheter to steer around, providing the danger of slippage and puncturing the opposite wall. As a result, the majority of patients, especially those with advanced degeneration or herniation, cannot be treated with this approach.

SUMMARY OF THE INVENTION

It is therefore an object of the invention to provide a treatment device which provides a significant improvement both in the thermal capabilities and therapeutic effects for disc tissue.

It is another object of the invention to provide a treatment device which can be used on an increased percentage of the potential treatment population and disease states.

It is yet another object of the invention to provide an ultrasound device that can effectively heat an increased volume of tissue for greater therapeutic effect.

It is still another object of the invention to provide an ultrasound device and treatment approach that allows for treatment during more advanced stages of disc degeneration.

It is finally another object of the invention to provide a robust design for an ultrasound device during insertion while also providing for improved directional control.

Further advantages and features of the present invention will be apparent from the following specifications and claims illustrating the preferred embodiments of the present invention.

DETAILED DESCRIPTION OF THE INVENTION

Figure 1:
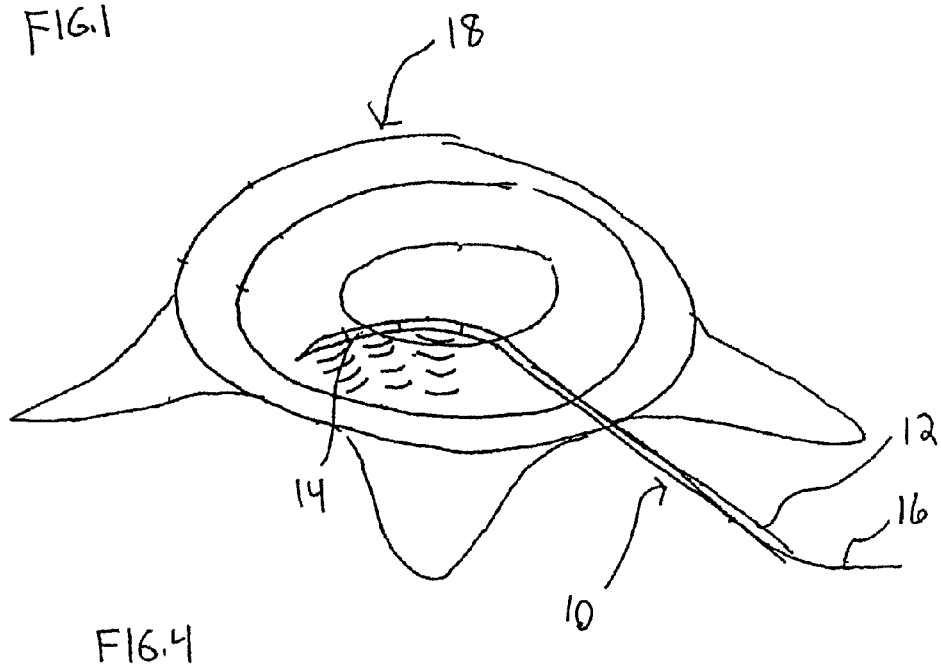
FIG. 1 is a perspective view of the ultrasound device according to one embodiment of the invention as it is positioned and maneuvered within the spinal body.

The present invention includes an applicator comprising a catheter and/or a needle with a distal tip for direct insertion into the tissue of the intervertebral disc. At the distal tip of the applicator is one or more ultrasound transducer crystals for producing high-powered ultrasound energy to be transmitted and absorbed in the disc tissue. In one embodiment of the invention, energy for the ultrasound transducer(s) is produced by an external RF power generator and delivered through electrical wires connected to the applicator. Small thermocouples can be placed on the ultrasound transducer/applicator and/or in the surrounding tissue to monitor the temperature. Means are also provided for active cooling of the ultrasound transducers by circulating flow of liquid or gas within the applicator.

The treatment process is initiated with the placement of the applicator device into the posterior region of the intervertebral disc tissue. The positioning of the applicator to the selected region of disc degeneration is guided via on-line diagnostic imaging, such as intra-operative fluoroscopic imaging. Power to the ultrasound device is then produced at a level to provide significant temperature elevation of the surrounding disc tissue. In one embodiment of the invention, the temperature elevation is greater than 60° C. for the targeted tissue. The temperature elevation is intended to shrink the collagen fibers in the surrounding tissue of the annulus fibrosus, and/or destroy small nerves that may have invaded and innervated the surrounding degenerated tissue, and/or provide greater structural integrity and disc support for the fragmented nucleus pulposus to relieve pressure on the spinal nerves.

Although these therapeutic effects are intended primarily for treatment of disc degeneration and herniation, this treatment approach with the ultrasound device may also be useful for other symptomatic spinal problems causing back pain, leg pain, etc. Additionally, the ultrasound device may be used to thermally shrink and/or seal the entrance hole and any subsequent unwanted tissue damage upon removal of the applicator from the disc tissue. In another embodiment of the device, the ultrasound transducers may also be used for diagnostic imaging to guide and monitor the treatment process.

The improvements described herein result primarily from the fundamental advantages of ultrasound propagation and heating of soft tissue. The effective energy delivery into the tissue allows for thermal treatment of larger tissue volumes in shorter times. Furthermore, the ultrasound device can be designed to provide selective control of the energy delivery to target and treat a specific region of tissue, dynamically controlling both the size and shape of the thermal treatment region. Extensive research and development activities have previously been completed on such ultrasound devices, and prototype applicators prepared for clinical application have demonstrated the feasibility of this approach.

FIG. 1 shows the ultrasound device positioned in the spinal body according to one embodiment of the invention. The ultrasound device, shown generally at 10, comprises a catheter or needle 12 with a plurality of ultrasound transducer crystals 14 at one end thereof. A guidewire 16 can be placed within the catheter or needle 12 for controlling the direction of the ultrasound device 10 inside the spinal body, shown generally at 18.

Figure 2:
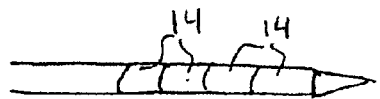
FIG. 2 is a side view of a plurality of segmented transducer elements with individual power control according to one embodiment of the invention.
Figure 3:
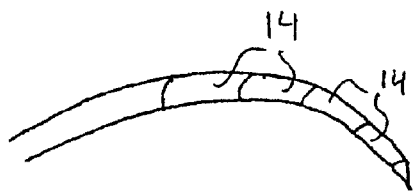
FIG. 3 is a side view of an alternate embodiment of the invention showing a curved array of transducer elements.

FIGS. 2-3 show different embodiments of the individual transducer crystals 14. FIG. 2 shows a plurality of segmented transducer crystals 14. Depending upon the particular system and procedure requirements, it is possible for each of the transducer crystals 14 to have individual power control. The embodiment shown in FIG. 3 discloses a curved array of transducer crystals 14. It is possible for the array of transducer crystals 14 to be permanently curved. Alternatively, the array could be flexible based upon the direction and shape of the guidewire 16.

Figure 4:
FIG. 4 is a cross-sectional view of a transducer element according to one embodiment of the invention.
Figure 5:
FIG. 5 is a cross-sectional view of a transducer element according to another embodiment of the invention.
Figure 6:
FIG. 6 is a cross-sectional view of an individual transducer element according to yet another embodiment of the invention.

FIGS. 4-6 show different potential cross-sectional shapes for the transducer crystals 14. FIG. 4 discloses a transducer crystal 14 with a cylindrically shaped cross-section. It is possible for the transducer crystal 14 to include or not include angular sectoring. FIG. 5 shows the transducer crystal as having a curvi-linear cross-section. This transducer crystal 14 could have a focused or defocused cross-section, depending on the direction of activation of ultrasound energy. The transducer crystal of FIG. 6 has a substantially planar cross-section. Transducer crystals 14 having cross-sections of other shapes are also possible without departing from the invention's broader aspects.

Additionally, the ultrasound device 10 could use a cooling method, either actively or passively, in order to remove thermal waste energy from the transducer crystal and improve the device's power and performance.

While the preferred embodiments of the invention have been described, it will be understood by those skilled in the art to which the invention pertains that numerous modifications and changes may be made without departing from the true spirit and scope of the invention. It is accordingly intended to define the scope of the invention precisely in the claims appended to and forming a part of this application.

The invention claimed is:

1. A minimally invasive applicator device for treatment of a tumor in a region of vertebral tissue, comprising:

an insertion device having a proximal end and a distal end for insertion into the tumor tissue, the insertion device being structurally robust for direct insertion into a targeted area of intervertebral disc tissue without damage or misalignment;

an ultrasound transducer device coupled to the distal end of the applicator wherein the ultrasound transducer device includes an array of a plurality of transducer crystals arranged in a straight line defined by an axis enclosed by each of the plurality of transducer crystals disposed sequentially and longitudinally adjacent each other along the axis to form a customized flexible array along the applicator device, thereby enabling ultrasound radiative output treatment outward from the axis of the transducer crystals of an extended region of specific size and shape of the intervertebral disc tissue; and an external RF power generator electrically connected to the ultrasound transducer device, the generator providing power to the ultrasound transducer device, wherein each of the plurality of transducer crystals has a non-circular cross-section.

2. The applicator device of claim 1, wherein the insertion device comprises a catheter or needle.

3. The device of claim 2, wherein the ultrasound transducer device includes at least one individual electrical power connection and control element.

4. The device of claim 3, wherein the plurality of transducer crystals include an individual electrical power connection.

5. The device of claim 2, further comprising means to cool internal transducer heating from the plurality of transducer crystals by circulating a flow of a liquid or gaseous coolant through the applicator device.

6. The device of claim 2, wherein the ultrasound transducer crystal is capable of being used to provide positioning visualization ultrasound imaging of the intervertebral disc tissue and surrounding tissue.

7. The device of claim 1, wherein each of the plurality of ultrasound transducer crystals are planar.

8. The device of claim 1, wherein the plurality of ultrasound transducer crystals are sectioned electrically and/or mechanically to provide separate active elements within at least one of the ultrasound transducer crystals.

9. The device of claim 1, further comprising a thermocouple placed on or adjacent to at least one of the ultrasound transducer crystals, the thermocouple monitoring the surface temperature of the device and/or the temperature of the tissue/device interface.

10. The device of claim 1, further comprising a thermocouple placed within the tissue to monitor the temperature of the treatment region of the intervertebral disc tissue.

11. The device of claim 10, wherein the thermocouple is deployed into the intervertebral disc tissue from the applicator.

12. The device of claim 1, further comprising a separate insertion tool or sheath for introduction into the intervertebral tissue containing tumor, and wherein the applicator is inserted into the tissue through the lumen of the insertion tool or sheath.

13. The device of claim 12, wherein the insertion tool comprises a predetermined fixed shape, and wherein the applicator is flexible to accommodate the fixed shape in its passage into the intervertebral disc tissue.

14. The device of claim 1, wherein the distal end of the applicator device is fixedly curved to provide enhanced accessibility of the ultrasound transducer to the posterior region of the intervertebral disc.

15. The device of claim 1, wherein the region is a diseased region.

16. The device of claim 1, wherein each of the plurality of ultrasound transducer crystals has a rectangular cross-section.

17. A method for treating a tumor associated with vertebral tissue in an extended-volume, thermal treatment region, comprising the steps of:
- inserting, positioning, and guiding an applicator device into tumor tissue via diagnostic imaging with the applicator device comprising a plurality of ultrasound transducer crystals having controlled size and shape to generate a custom size and shape for the extended volume thermal treatment region wherein the plurality of ultrasound transducer crystals are arranged in a straight line defined by a longitudinal axis of the plurality of transducer crystals disposed sequentially adjacent each other along the axis, wherein each of the plurality of transducer crystals has a non-circular cross-section;
- applying power to at least one ultrasound transducer of the applicator device, the at least one ultrasound transducer heating the treatment region of the tumor tissue associated with vertebral tissue;
- removing the applicator device from the tumor tissue.

18. The method of claim 17, wherein the applicator is positioned and guided using at least one of intra-operative fluoroscopic imaging and one of diagnostic ultrasound imaging.

19. The method of claim 17, wherein the diagnostic imaging comprises ultrasound imaging provided by the transducer crystals located within the applicator device.

20. The method of claim 17, further comprising the step of measuring the temperature on the applicator and/or in the surrounding tissue wherein the temperature sensor is integrated with the applicator.

21. The method of claim 17, further comprising the step of heating an entrance hole with the applicator device in order to produce thermal sealing or shrinking of the tissue upon removal of the applicator.

22. The method of claim 17, wherein the transducer heating is controlled by varying the power, frequency, or duration of the applied signal to each of the transducer crystals.

23. The method of claim 17, further comprising the step of delivering a drug or therapeutic agent into the intervertebral disc tissue to enhance the therapeutic effect of the thermal energy delivery.

* * * * *